(12) United States Patent
Geheb et al.

(10) Patent No.: US 7,190,999 B2
(45) Date of Patent: Mar. 13, 2007

(54) CARDIO-PULMONARY RESUSCITATION DEVICE WITH FEEDBACK FROM MEASUREMENT OF PULSE AND/OR BLOOD OXYGENATION

(75) Inventors: Frederick Geheb, Danvers, MA (US); Donald R. Boucher, Andover, MA (US)

(73) Assignee: Zoll Medical Corporation, Chelmsford, MA (US)

( * ) Notice: Subject to any disclaimer, the term of this patent is extended or adjusted under 35 U.S.C. 154(b) by 448 days.

(21) Appl. No.: 10/609,001

(22) Filed: Jun. 27, 2003

(65) Prior Publication Data

US 2004/0267324 A1    Dec. 30, 2004

(51) Int. Cl.
*A61N 1/00* (2006.01)

(52) U.S. Cl. .............................. 607/5; 600/515; 601/41
(58) Field of Classification Search .................. 607/5, 607/19, 20; 600/382, 502
See application file for complete search history.

(56) References Cited

U.S. PATENT DOCUMENTS

| | | | |
|---|---|---|---|
| 4,059,099 A | 11/1977 | Davis | |
| 4,355,634 A | 10/1982 | Kanter | |
| 4,588,383 A * | 5/1986 | Parker et al. | 434/265 |
| 4,863,385 A * | 9/1989 | Pierce | 434/265 |
| 5,020,516 A | 6/1991 | Biondi et al. | |
| 5,496,257 A | 3/1996 | Kelly | |
| 6,125,299 A | 9/2000 | Groenke et al. | |
| 6,174,295 B1 | 1/2001 | Cantrell et al. | |
| 6,201,992 B1 * | 3/2001 | Freeman | 607/5 |
| 6,306,107 B1 | 10/2001 | Myklebust et al. | |
| 6,390,996 B1 * | 5/2002 | Halperin et al. | 601/41 |
| 6,427,685 B1 | 8/2002 | Ray, II | |
| 6,827,695 B2 | 12/2004 | Palazzolo et al. | |
| 6,872,080 B2 * | 3/2005 | Pastrick et al. | 434/262 |
| 6,961,612 B2 * | 11/2005 | Elghazzawi et al. | 607/6 |
| 2001/0047140 A1 | 11/2001 | Freeman | |
| 2002/0165585 A1 | 11/2002 | Dupelle et al. | |
| 2003/0028219 A1 | 2/2003 | Powers et al. | |

FOREIGN PATENT DOCUMENTS

| | | |
|---|---|---|
| EP | 1057451 A2 | 12/2000 |
| WO | 98/55015 | 12/1998 |
| WO | 02/15836 A2 | 2/2002 |
| WO | 02/091905 | 11/2002 |

OTHER PUBLICATIONS

U.S. Appl. No. 10/421,652 (Marcovecchio, Optical Pulse Sensor for External Defibrillator).

(Continued)

*Primary Examiner*—Robert E. Pezzuto
*Assistant Examiner*—Brian T. Gedeon
(74) *Attorney, Agent, or Firm*—Fish & Richardson P.C.

(57) ABSTRACT

An apparatus for assisting a rescuer in performing CPR on a victim. The apparatus comprising at least one of a pulse sensor for measuring the pulse rate of the victim and an SpO2 sensor for measuring blood oxygenation; electronics for processing the output of the sensor or sensors and determining one or more actions that the rescuer should perform to improve the CPR being performed; and a prompting device for conveying the one or more actions to the rescuer.

22 Claims, 3 Drawing Sheets

OTHER PUBLICATIONS

U.S. Appl. No. 10/370,036 (Elghazzawi et al., CPR Sensitive ECG Analysis in an Automatic External Defibrillator).

U.S. Appl. No. 10/441,933 (Marcovecchio, Processing Pulse Signal in Conjunction with ECG Signal.

Aase et al., "CPR Artifact Removal from Human ECG Using Optimal Multichannel Filtering," IEEE Transactions on Biomedical Engineering, vol. 47, 1440-1449, (2000).

Eftestol et al., "Effects of Interrupting Precordial Compressions on the Calculated Probability of Defibrillation Success During Out-of-Hospital Cardiac Arrest," Circulation, 105, 2270-2273, (2002).

Haykin, Adaptive Filter Theory, Third Edition, Upper Saddle River, NJ, USA. Prentice-Hall, 1996.

Husoy et al., "Removal of Cardiopulmonary Resuscitation Artifacts from Human ECG Using an Efficient Matching Pursuit-Like Algorithm," IEEE Transactions on Biomedical Engineering, vol. 49, 1287-1298, (2002).

Langhelle et al. "Reducing CPR Artifacts in Ventricular Fibrillation in Vitro," Resuscitation. Mar; 48(3):279-91 (2001).

Sato et al., "Adverse effects of interrupting precordial compression during cardiopulmonary resuscitation," Critical Care Medicine, vol. 25(5), 733-736 (1997).

Yu et al., "Adverse Outcomes of Interrupted Precordial Compression During Automated Defibrillation," Circulation, 106, 368-372 (2002).

\* cited by examiner

CARDIO-PULMONARY RESUSCITATION DEVICE WITH FEEDBACK FROM MEASUREMENT OF PULSE AND/OR BLOOD OXYGENATION

RELATIONSHIP TO OTHER APPLICATIONS

The following copending applications are incorporated by reference: U.S. Ser. No. 10/370,036, filed on Feb. 19, 2003; U.S. Ser. No. 09/794,320, filed on Feb. 27, 2001; U.S. Ser. No. 10/421,652, filed on Apr. 23, 2003; U.S. Ser. No. 09/846,673, filed on May 1, 2001; and U.S. Ser. No. 10/441,933, filed on May 20, 2003.

TECHNICAL FIELD

This invention relates to devices for assisting cardiac resuscitation.

BACKGROUND

This invention relates to the field of cardiac resuscitation, and in particular to devices for assisting rescuers in performing cardio-pulmonary resuscitation (CPR). CPR is used to mechanically support circulation in subjects with cardiac arrest. Although, the American Heart Association (AHA) has proposed guidelines for CPR, the effectiveness of this intervention is difficult to actively assess as it is performed. The ZOLL Medical AED Plus system provides rescuers with valuable feedback on compression rate (metronome) and depth (audible prompts) to promote the proper CPR methodology.

SUMMARY

I have discovered that improved feedback can be provided to a rescuer providing CPR by providing adjustments to the metronome and additional audible prompts based on the effectiveness of the CPR on the victim's circulation as measured by pulse rate and SpO2 from oximetry.

In a first aspect, the invention features an apparatus for assisting a rescuer in performing CPR on a victim. The apparatus comprises at least one of a pulse sensor for measuring the pulse rate of the victim and an SpO2 sensor for measuring blood oxygenation; electronics for processing the output of the sensor or sensors and determining one or more actions that the rescuer should perform to improve the CPR being performed; and a prompting device for conveying the one or more actions to the rescuer.

Preferred implementations of this aspect of the invention may incorporate one or more of the following. The apparatus may further comprise an external defibrillator. The apparatus may comprise an SpO2 sensor but not a pulse sensor. The apparatus may comprise a pulse sensor but not an SpO2 sensor. The apparatus may further comprise a chest compression sensor. The chest compression sensor may be an acclerometer. The electronics may be provided with information on compression rate. The compression rate may be sensed or derived from a chest compression sensor. The prompting device may comprise a device that conveys a desired rate of compression to the rescuer. The device that conveys a desired rate of compression to the rescuer may comprise a metronome. The prompting device may comprise a speaker and associated electronics for conveying audible instructions. The electronics may comprise a digital computer executing computer software. The electronics may compare compression rate to a desired CPR rate. The electronics may compare a measured level of blood oxygenation to a desired level. The electronics may provide a prompt instructing the rescuer to release from the chest during CPR delivery if the sensors indicate that the rescuer is not adequately releasing from the chest. The electronics may provide a prompt to the user to press harder if the pulse sensor indicates that there is no measured pulse rate. The electronics may provide a prompt to press harder if the sensor indicate that a pulse is detected but SpO2 is below a defined level. The electronics may provide a prompt to increase compression rate if the sensors indicate that a pulse is detected, that chest compressions are at a defined level, and that SpO2 is still below a defined level. The electronics may provide prompts to increase compression rate and compression pressure simultaneously based on measurements from sensors. The electronics may provide a prompt for the user to interrupt chest compressions to give one or more breaths. The prompt to give one or breaths may be issued when sensor measurements show that blood circulation is occurring and that the cause of a falling SpO2 level may be an increase in metabolism. The electronics may provide a prompt to continue CPR without interruption for breathing based on SpO2 levels that were above a given threshold so as to ensure that there would be no break in circulation when blood oxygen levels remained high and ventilation was not yet required.

Other features and advantages of the invention will be apparent from the following detailed description, and from the drawings and claims.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

Figure 1:
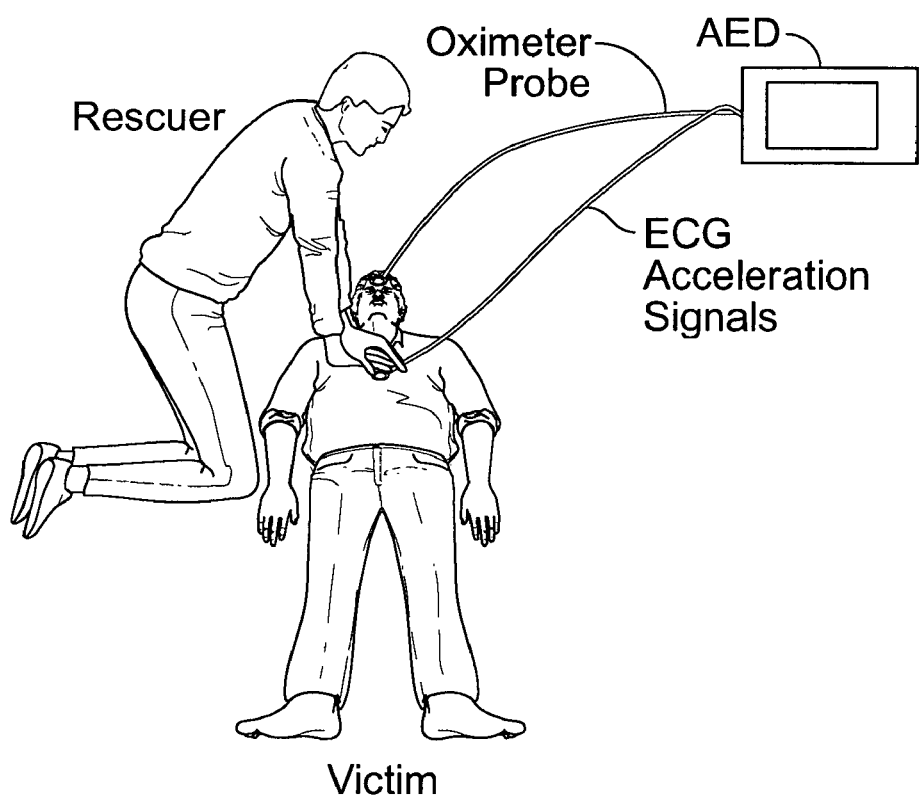
FIG. 1 is a diagrammatic view of a rescuer providing CPR to a victim with the aid of an implementation of the invention.
Figure 2:
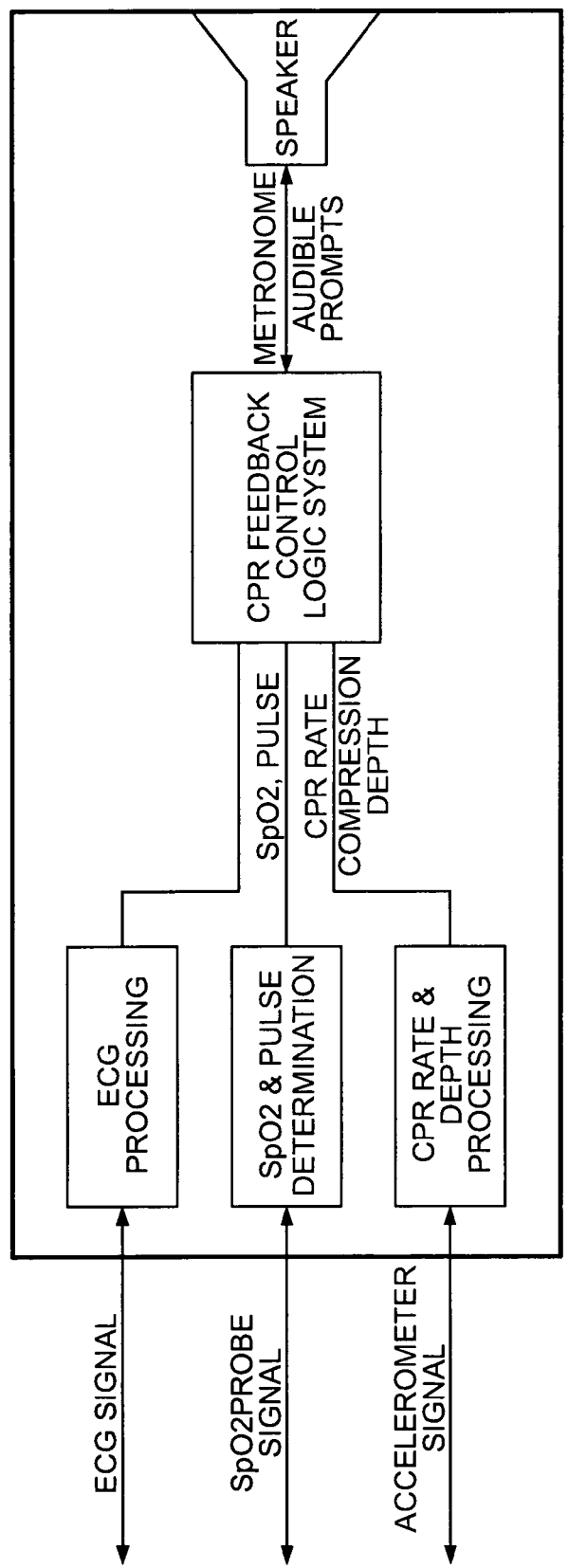
FIG. 2 is a block diagram of an implementation of the invention.

The descriptions below are more than sufficient for one skilled in the art to construct the disclosed implementations. Unless otherwise mentioned, the processes and manufacturing methods referred to are ones known by those working in the art FIGS. 1–2 show an AED implementation of the invention that can measure CPR rate and depth with an accelerometer, and SpO2 and pulse rate with an oximeter probe (FIG. 1). These measures are provided as inputs to a software module, which assesses whether the CPR is producing adequate pulse rate and oxygenation (FIG. 2). The SpO2 sensor can be located in various locations, e.g., on the finger to provide measurements on the peripheral circulation and/or on the forehead to reflect cerebral circulation.

Figure 3:
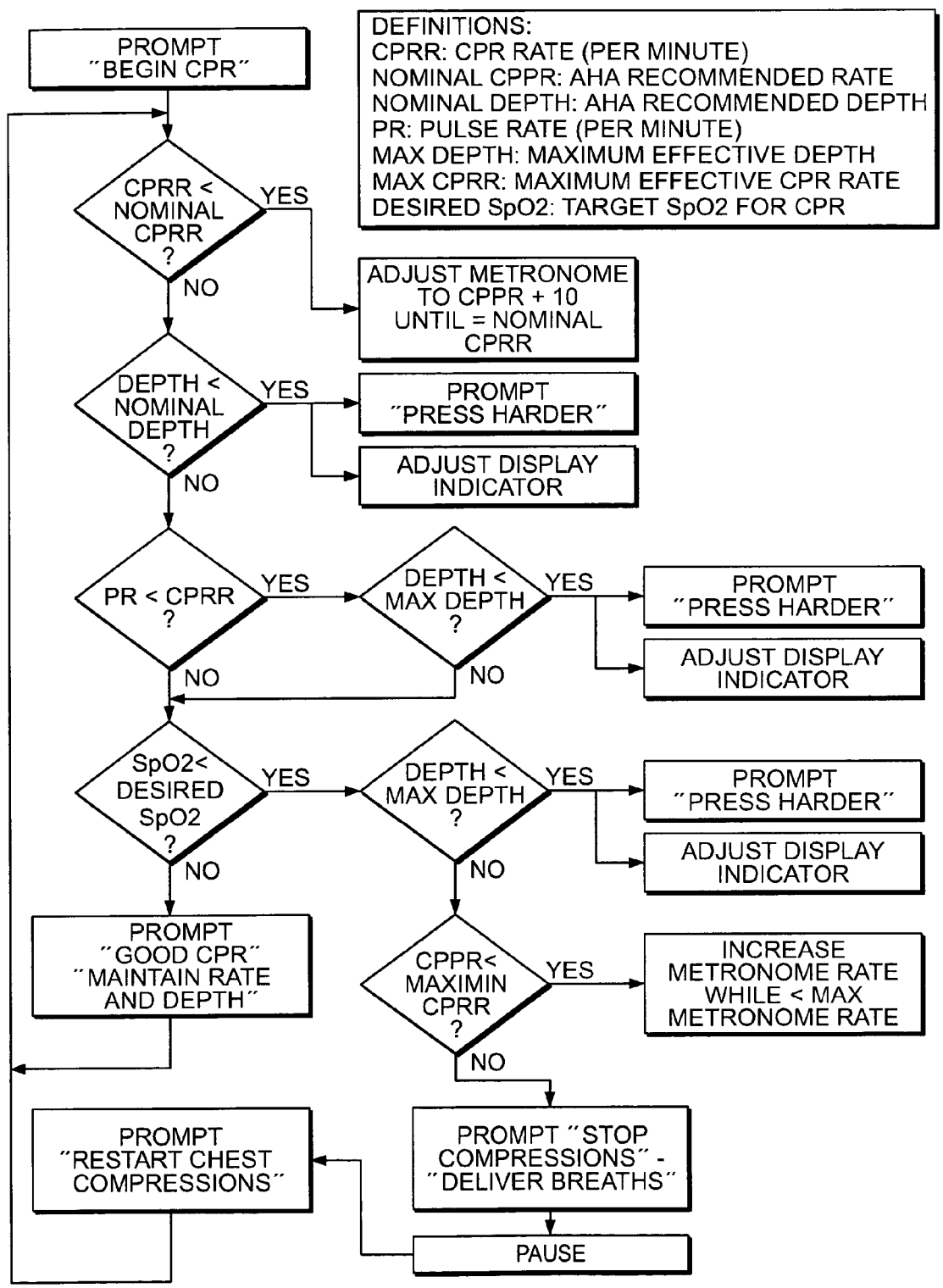
FIG. 3 is a flow chart of the operation of an implementation of the invention.

The user is initially prompted with the use of a metronome (i.e., a rate indicating prompt) and audible instructional prompts to perform CPR optimally according to AHA guidelines (100 cpm, 1.5–2.0 inch compression). Based on the current compression rate, compression depth, SpO2 measurement, and pulse rate, the compression rate and compression depth can be altered from the recommended guideline via the metronome and voice prompts to improve circulation. For example, the feedback control system via the AED metronome and audible prompts can operate with the user in the following ways based on the state of the CPR and the state of the patient (FIG. 3):

1. If a pulse rate is measured that matches the CPR rate and the SpO2 has reached a defined level, CPR may be considered adequate and no changes to the metronome or additional voice prompts may be required.

2. The user may be prompted to release the chest if the CPR system has determined that the chest is not being completely released at the end of each compression.

3. If there is no pulse rate from the oximeter, the user may be prompted to pressure harder until the pulse rate is detected.

4. If there is a detected pulse rate and the SpO2 level has not reached a defined level, the user may be prompted to press harder to increased in the oxygen saturation.

5. If the increase in compression depth meets a safe maximum and does not achieve the desired SpO2 level (in item 3), the metronome rate can be increased to a safe maximum rate to increase saturation.

6. Based on the current state of the compression rate and depth and the pulse rate and SpO2, both the metronome rate and the compression prompts can be used simultaneously to more quickly move to a desired operating point.

7. The user may be prompted to continue CPR without interruption for breathing based on SpO2 levels that were above a given threshold. This would ensure that there would be no break in circulation when blood oxygen levels remained high and ventilation was not yet required. There is literature which indicates that within an initial period following collapse there is sufficient oxygen reserve in the blood that ventilation is not necessary and CPR should not be interrupted. Monitoring the SpO2 and guiding the user through audible prompts would suppress breathing and direct uninterrupted CPR.

The feedback system may, also, be used to prompt the rescuer to deliver rescue breathing when chest compression depth and rate are appropriate but arterial blood oxygen saturation is falling from a previously higher level. This condition may indicate that although chest compressions are adequate to circulate blood, the level of blood oxygen has diminished due to metabolism and additional oxygen delivery (accomplished by rescue breathing) is required to improve the victim's condition. Based upon detection of this set of conditions, the feedback control system will issue audible prompts instructing the rescuer to stop compressions for a brief period and deliver one or several rescue breaths. The system will then prompt the rescuer to resume chest compressions as it monitors CPR, pulse and oxygen saturation parameters to estimate the success of CPR efforts and provide further prompts related to compression rate, depth and breathing.

Similarly, if the pulse oximetry sensor detects an increase from a lower level to a higher level of blood oxygen saturation in peripheral tissues during CPR, the feedback control system may determine that CPR is being effectively delivered. Under these conditions, the system will continue prompting the rescuer to maintain his/her rate and depth of chest compressions until the oxygen saturation plateaus and/or begins to decrease. When this occurs, the feedback system may (based upon detected compression rate, depth, pulse rate and blood oxygen saturation) prompt the rescuer to change his/her chest compression depth or rate or alternatively recommend the delivery of rescue breaths to the victim.

The system is designed as a feedback control system utilizing program logic (FIG. 3), or linear and/or non-linear optimization techniques focused on maximizing the SpO2 as the cost function.

The CPR rate and depth measures can be used to ensure the control system remains within reasonable bounds based on predefined compression rate and depth ranges. These ranges are determined based on the established range for effective CPR.

Many other implementations of the invention other than those described above are within the invention, which is defined by the following claims. For example, other types of sensors could be used to provide SpO2 and pulse rate; each could be measured by a separate sensor. In some implementations, only one or the other of the parameters could be measured and used as the basis for feedback to the rescuer. The term SpO2 sensor has been used herein, but it should be understood that any sensor that provides a measure of blood oxygenation or pulmonary function is within what is meant by SpO2 sensor. Similarly, the pulse sensor can be any of various types that detect pulsatile movement of blood in the circulatory system (e.g., pulse oximetry based pulse sensors, piezoelectric sensors, etc.).

What is claimed is:

1. Apparatus for assisting a rescuer in performing CPR on a victim, the apparatus comprising:
    at least one of a pulse sensor for measuring the pulse rate of the victim and an SpO2sensor for measuring blood oxygenation;
    electronics for processing the output of the sensor or sensors and determining one or more actions that the rescuer should perform to improve delivery of chest compressions; and
    a prompting device for conveying the one or more actions to the rescuers,
    wherein the actions conveyed to the rescuer to improve chest compressions include at least one of the following (1) changing the rate at which the rescuer delivers chest compressions and (2) changing the pressure applied to the chest.

2. The apparatus of claim 1 further comprising an external defibrillator.

3. The apparatus of claim 1 wherein the apparatus comprises an SpO2 sensor but not a pulse sensor.

4. The apparatus of claim 1 wherein the apparatus comprises a pulse sensor but not an SpO2 sensor.

5. The apparatus of claim 1 further comprising a chest compression sensor.

6. The apparatus of claim 5 wherein the chest compression sensor is an accelerometer.

7. The apparatus of claim 1 wherein the electronics is provided with information on compression rate.

8. The apparatus of claim 7 wherein the compression rate is sensed or derived from a chest compression sensor.

9. The apparatus of claim 1 wherein the prompting device comprises a device that conveys a desired rate of compression to the rescuer.

10. The apparatus of claim 9 wherein the device that conveys a desired rate of compression to the rescuer comprises a metronome.

11. The apparatus of claim 1 wherein the prompting device comprises a speaker and associated electronics for conveying audible instructions.

12. The apparatus of claim 1 wherein the electronics comprises a digital computer executing computer software.

13. The apparatus of claim 1 wherein the electronics compares compression rate to a desired CPR rate.

14. The apparatus of claim 1 wherein the electronics compares a measured level of blood oxygenation to a desired level.

15. The apparatus of claim 1 wherein the electronics provides a prompt instructing the rescuer to release from the chest during CPR delivery if the sensors indicate that the rescuer is not adequately releasing from the chest.

16. The apparatus of claim 1 wherein the electronics provides a prompt to the user to press harder if the pulse sensor indicates that there is no measured pulse rate.

17. The apparatus of claim 1 wherein the electronics provides a prompt to press harder if the sensor indicate that a pulse is detected but SpO2 is below a defined level.

18. The apparatus of claim 1 wherein the electronics provides a prompt to increase compression rate if the sensors indicate that a pulse is detected, that chest compressions are at a defined level, and that SpO2 is still below a defined level.

19. The apparatus of claim 1 wherein the electronics provides prompts to increase compression rate and compression pressure simultaneously based on measurements from sensors.

20. The apparatus of claim 1 wherein the electronics provides a prompt for the user to interrupt chest compressions to give one or more breaths.

21. The apparatus of claim 20 wherein the prompt to give one or more breaths is issued when sensor measurements show that blood circulation is occurring and that the cause of a falling SpO2 level may be an increase in metabolism.

22. The apparatus of claim 1 wherein the electronics provide a prompt to continue CPR without interruption for breathing based on SpO2 levels that were above a given threshold so as to ensure that there would be no break in circulation when blood oxygen levels remained high and ventilation was not yet required.

* * * * *